United States Patent [19]
Kunze

[11] Patent Number: 5,370,829
[45] Date of Patent: Dec. 6, 1994

[54] APPARATUS FOR INDUCING AIR FLOW PAST A CARTRIDGE CONTAINING A VAPORIZABLE SUBSTANCE

[75] Inventor: Walter A. Kunze, Southington, Conn.

[73] Assignee: Waterbury Companies, Inc., Waterbury, Conn.

[21] Appl. No.: 138,123

[22] Filed: Oct. 15, 1993

[51] Int. Cl.⁵ .............................................. B01F 3/04
[52] U.S. Cl. ...................................... 261/24; 261/99; 261/DIG. 65; 422/124
[58] Field of Search .................. 261/DIG. 65, 24, 99; 422/124

[56] References Cited

U.S. PATENT DOCUMENTS

| | | | |
|---|---|---|---|
| 2,629,149 | 2/1953 | Yaffe | 422/124 |
| 3,908,905 | 9/1975 | Philipp et al. | 239/55 |
| 3,990,848 | 11/1976 | Corris | |
| 3,993,444 | 11/1976 | Brown | 261/DIG. 65 |
| 4,065,261 | 12/1977 | Fukada | 261/DIG. 65 |
| 4,166,087 | 8/1979 | Cline | 261/DIG. 65 |
| 4,271,092 | 6/1981 | Sullivan et al. | |
| 4,370,300 | 1/1983 | Mori et al. | 422/124 |
| 4,666,638 | 5/1987 | Baker et al. | 261/DIG. 65 |
| 4,743,406 | 5/1988 | Steiner et al. | |
| 4,830,791 | 5/1989 | Muderlak et al. | |
| 4,840,770 | 6/1989 | Walz et al. | |
| 4,865,816 | 9/1989 | Walz et al. | |
| 4,931,258 | 6/1990 | Zlotnik et al. | 422/124 |
| 5,147,582 | 9/1992 | Holzner, Sr. et al. | 261/DIG. 65 |
| 5,230,867 | 7/1993 | Kunze et al. | |

FOREIGN PATENT DOCUMENTS 0267697 5/1988 European Pat. Off. .... 261/DIG. 65

Primary Examiner—Tim Miles
Attorney, Agent, or Firm—St. Onge Steward Johnston & Reens

[57] ABSTRACT

A dispenser having a housing and at least one inlet vent and at least one outlet vent about the housing is shown. A fan, preferably a centrifugal fan, is operated by a battery and directs air into and out of the vents. A cartridge containing a vaporizable substance, such as a fragrant oil or gel, is located adjacent the inlet vent. The centrifugal fan pulls air in the inlet vent, at least partially across the cartridge, upward through a portion of the housing, and radially outward through the outlet vent. Preferably, a rim of the cartridge and a shelf inside the housing and adjacent the rim are adapted to form substantially a boundary between a lower and a middle compartment in the housing. The shelf and the rim cooperate to prevent air from circulating below the shelf and entering the lower compartment. At least one upper rib and a housing of the fan are adapted to form a boundary between the middle compartment and an upper compartment. The fan housing and upper rib cooperate to prevent air from entering the upper compartment except through the fan. Preferably, a shield or a wall separates the fan from the battery such that the vaporized substance does not undesirably interfere with the electrical operation of the battery.

19 Claims, 5 Drawing Sheets

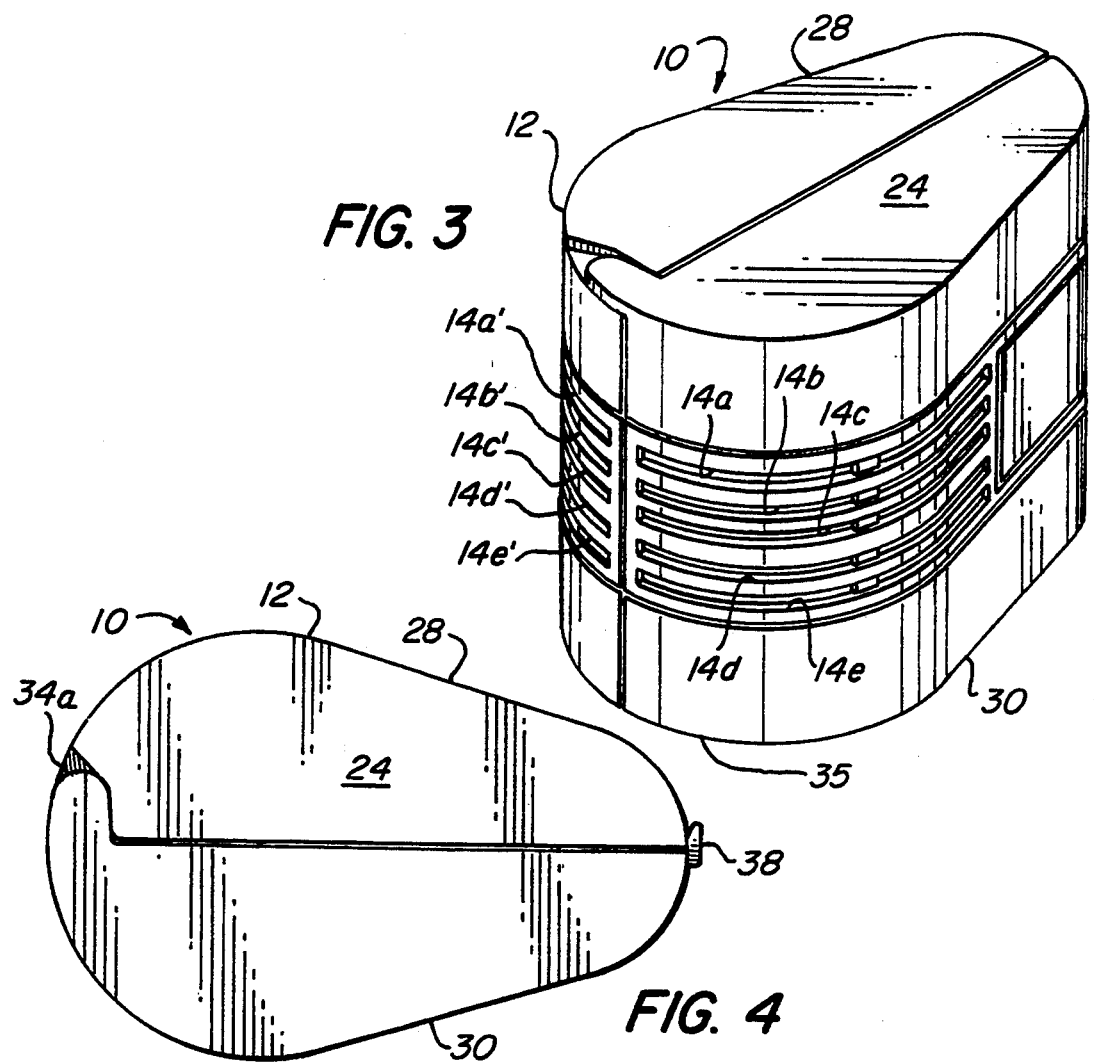
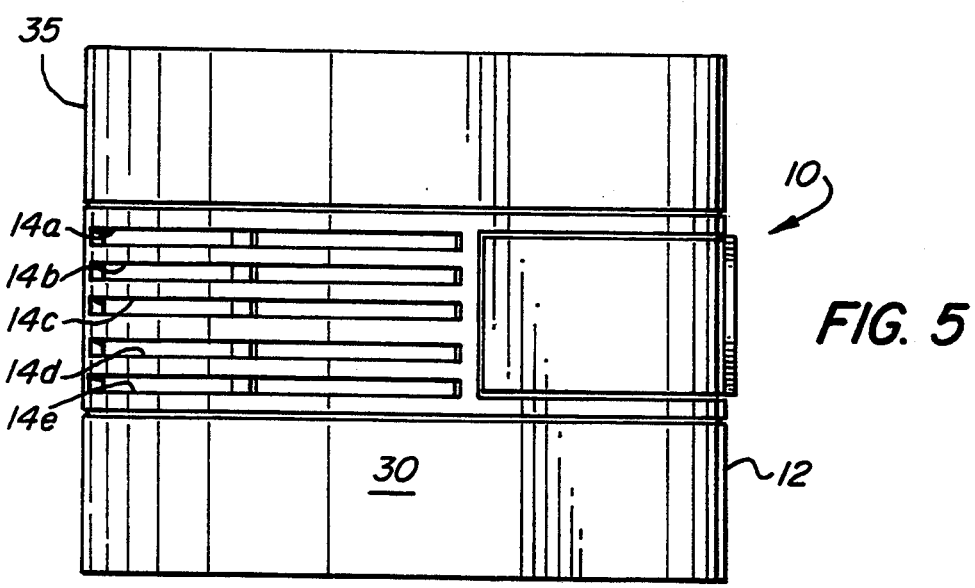

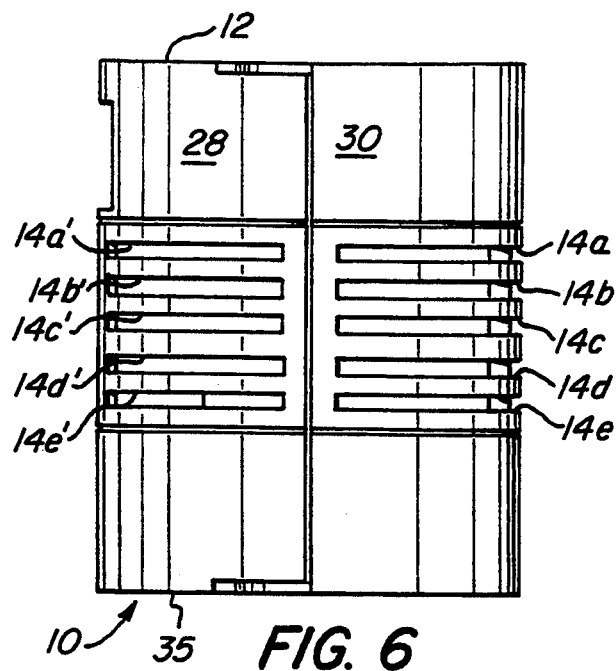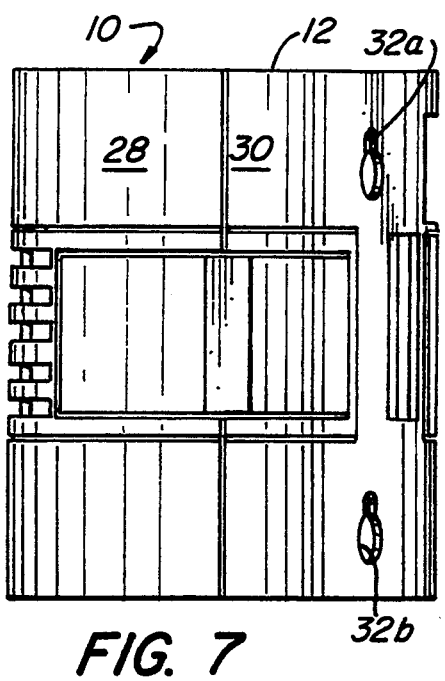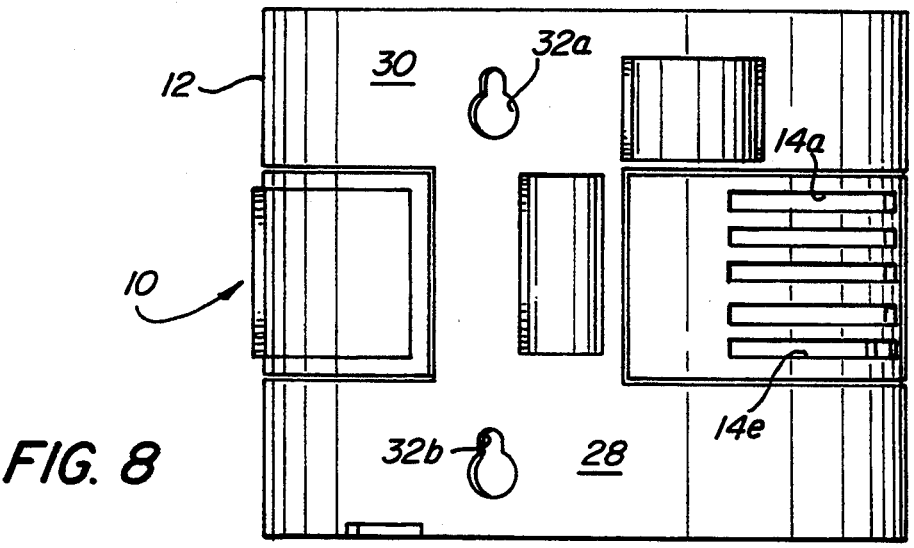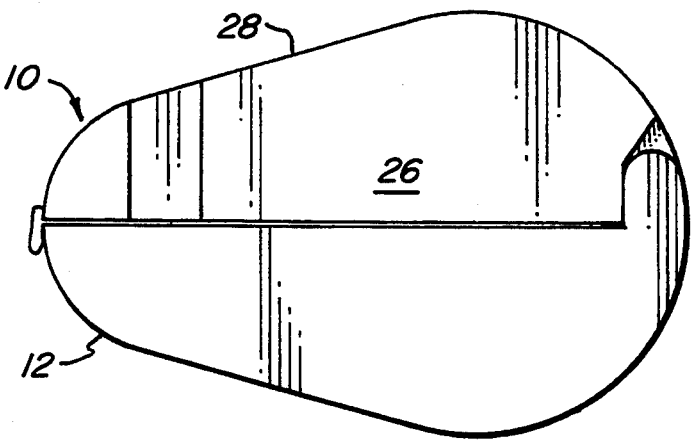

APPARATUS FOR INDUCING AIR FLOW PAST A CARTRIDGE CONTAINING A VAPORIZABLE SUBSTANCE

TECHNICAL FIELD

The present invention relates to devices for inducing air flow past a cartridge containing a vaporizable substance, such as a fragrant oil or gel, wherein the substance is released into the atmosphere to, for instance, overcome undesirable odors typically associated with public washrooms and the like.

It is known to provide a self-contained air freshener having a housing containing a battery-operated fan which blows air directly onto a cartridge containing a pleasant smelling oil or gel. The fan vaporizes the oil or gel into the surrounding atmosphere creating a desirable smell in the room.

One problem typically associated with these air fresheners is minimizing the size of the housing while maximizing the air flow past the cartridge containing the oil or gel, while still generating an effective odor for a relatively long period of time. Having a small housing is highly desirable, since a large housing is considered unsightly, yet having a smaller housing can compromise operation effectiveness. For example, a fan which blows air directly down onto the cartridge causes so much air to flow past the cartridge and the oil or gel that the oil or gel evaporates before it can be vaporized and generally requires a larger housing to place a sufficient distance between the fan and the cartridge. In addition, the rate of vaporization may be unacceptably high. As such, much oil or gel is wasted and the cartridge becomes empty long before the battery life has expired.

In order to reduce the amount of oil or gel which is vaporized, the fan must generally be moved farther from the oil or gel. While this reduces the amount of oil or gel which is evaporated and also reduces the rate vaporization, the housing size must be enlarged to increase the distance between the fan and the cartridge.

Other drawbacks are associated with known air fresheners. For example, some air fresheners do not provide a clear path for air flow between the oil containing cartridge and the fan. Some do not maximize the amount of air flow over the cartridge, because the fan is turned sideways. Others provide vents which are not adjacent to the fan or the cartridge, thus the deodorizing fragrance is sometimes lost or dissipated inside the housing. These known dispensers and others also undesirably allow the air containing the vaporized substance to flow into portions of the dispenser where the air can become trapped and the deodorizing effect is thus minimized.

What is desired, therefore, is a dispenser which is relatively small, which maximizes air flow by providing a plurality of vents which are located adjacent to the fan and the cartridge, which does not force air directly down onto the cartridge, which prohibits the undesirable flow of air by use of a compartment, or chamber, which channels air only into desirable dispenser portions, and which provides a clear path for air flow out of the housing to maximize the deodorizing effect.

SUMMARY OF THE INVENTION

Accordingly, it is an object of the present invention to provide a vaporizable substance dispenser which is reduced in size when compared to conventional dispensers, but which does not cause the vaporizable substance to evaporate so quickly as to be uneconomical.

It is another object of the invention to provide a vaporizable substance dispenser which pulls air upward from a cartridge, rather than directly onto the cartridge.

It is yet another object of the present invention to provide a vaporizable substance dispenser which has an unobstructed path of air flow and which maximizes the air flowing past the cartridge.

It is still a further object of the invention to provide a vaporizable substance dispenser which has at least one chamber substantially adjacent to a fan, vents, and the cartridge, the chamber having boundaries so as to impede undesirable air flow.

To overcome the deficiencies of the prior art and to achieve the objects and advantages listed above, Applicant discloses a dispenser having a housing containing at least one inlet vent and at least one outlet vent, a fan operated by a battery for directing air into and out of the vents, and a cartridge, containing a vaporizable substance, which is vaporized by the airflow generated by the fan and directed into the atmosphere through the outlet vents. Due to the arrangement of the fan, vents, and cartridge, air flow is generally through a chamber which is bounded partially by a fan housing and a cartridge rim.

In the preferred embodiment, there are a plurality of parallel and adjacent inlet and outlet vents. Most preferably, in order to maximize dispersal of the vaporizable substance, the vents extend approximately one hundred ninety degrees to two hundred thirty degrees about the perimeter of the housing. The lowermost vents are generally the inlet vents, while the uppermost vents are generally the outlet vents. In the preferred embodiment, the rim of the cartridge is located adjacent the inlet vents. The fan is located adjacent to the outlet vents.

Preferably, the rim of the cartridge and a shelf inside the housing and adjacent the rim are adapted to form a boundary between the middle and a lower compartment in the housing. Another shelf, or radial rib, extends outward from an inner wall of the housing adjacent the fan housing to form a boundary between the middle and an upper compartment. As such, three compartments, or cylindrical chambers, are formed wherein the middle compartment is adjacent the inlet vents. The shelf and the rim cooperate to prevent air from circulating below the shelf and entering the lower compartment. The upper rim cooperates with a housing of the fan to prevent the air from entering the upper compartment, except through the fan housing.

Preferably, a shield or a wall separates the fan from the battery such that the vaporized substance does not undesirably interfere with the electrical operation of the battery, nor is the substance wasted by being directed into the battery compartment.

The fan, which is most preferably a centrifugal fan, pulls air in the inlet vents, at least partially across the cartridge, upward through a portion of the housing, and radially outward through the outlet vents. As such, air flow is generally confined to the middle and upper chambers.

In the preferred embodiment, the cartridge and the battery are removable. As such, an expired cartridge and battery is easily replaced through a hinged door of the dispenser housing.

Other objects will become more readily apparent when the following description is read in conjunction with the accompanying drawings.

BRIEF DESCRIPTION OF THE DRAWINGS

FIG. 3 is an isometric view of the dispenser shown in FIG. 1, with the dispenser door attached;

FIG. 4 is a top view of the dispenser;

FIG. 5 is a front plan view of the dispenser;

FIG. 6 is a plan view of an end of the dispenser;

FIG. 7 is a plan view of the other end of the dispenser;

FIG. 8 is a rear plan view of the dispenser; and

FIG. 9 is a bottom plan view of the dispenser.

DETAILED DESCRIPTION OF THE DRAWINGS

Figure 1:
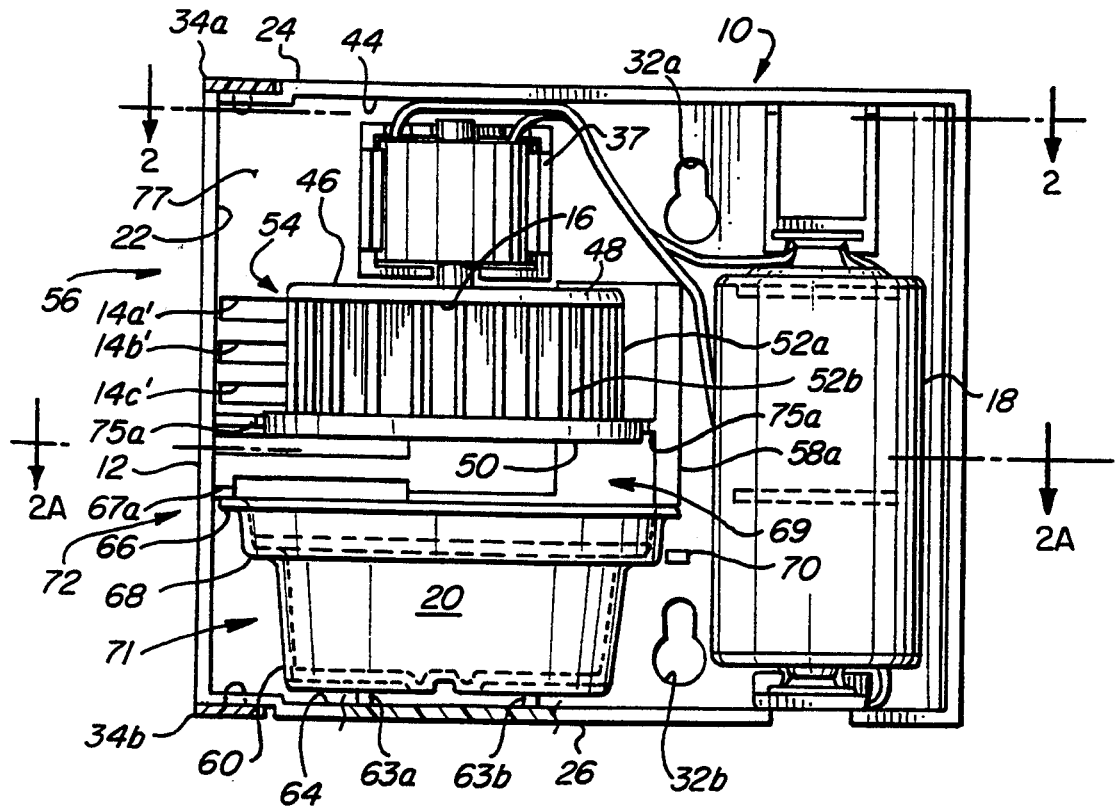
FIG. 1 is a front view of a dispenser in partial cross section housing a cartridge, constructed in accordance with the invention, wherein the dispenser door has been removed for clarity.

Referring to the drawings in detail, a self-contained vaporizable substance dispenser, constructed in accordance with the present invention, is shown and generally designated by the reference numeral 10. It should be noted that for the sake of clarity all the components and parts of dispenser 10 may not be shown and/or marked in all the drawings. Also, as used in this description, the terms "up", "down", "top", "bottom", etc. refer to dispenser 10 when in the orientation illustrated in FIG. 1. It should also be understood that dispenser 10 may be in any of various orientations when in use, and, as such, the orientation illustrated in FIG. 1 is not necessary for operability. Furthermore, as used in this description, the terms "front" and "back" also refer to dispenser 10 when in the orientation illustrated in FIG. 1, with "front" indicating that portion of dispenser 10 shown in FIG. 5 and "back" indicating that portion of dispenser 10 shown in FIG. 8.

Although this description is written in terms of dispensing a fragrant oil or gel, such description is for convenience only. It should be understood that the present invention applies to a dispenser for any vaporizable substance.

Dispenser 10 is generally comprised of housing 12 having a plurality of inlet and outlet vents 14a, 14b, 14c, 14d, 14e, 14a', 14b', 14c', 14d', 14e', fan 16 adjacent the vents, battery 18 for operating fan 16, and fragrance containing cartridge 20 adjacent the vents and in relation to fan 16, such that fan 16 pulls air in through at least one inlet vent, at least partially across cartridge 20, through housing 12 and radially outward through at least one outlet vent. See FIGS. 1, 2, 2A, 3.

Housing 12 can be made of any suitable material, such as plastic, like low- or high-density polyethylene, and can be made by any suitable method such as injection molding. Housing 12 includes an internal chamber 22 (shown in FIG. 1) defined by top 24 (shown in FIG. 4), bottom 26 (shown in FIG. 9), back side 28 (shown in FIG. 8) and front side 30 (shown in FIG. 5). Housing 12 can stand freely on bottom surface 26 or can be secured, as desired, to a wall (not shown), or other vertical surfaces by key holes 32a, 32b. See FIGS. 1, 8.

Figure 2:
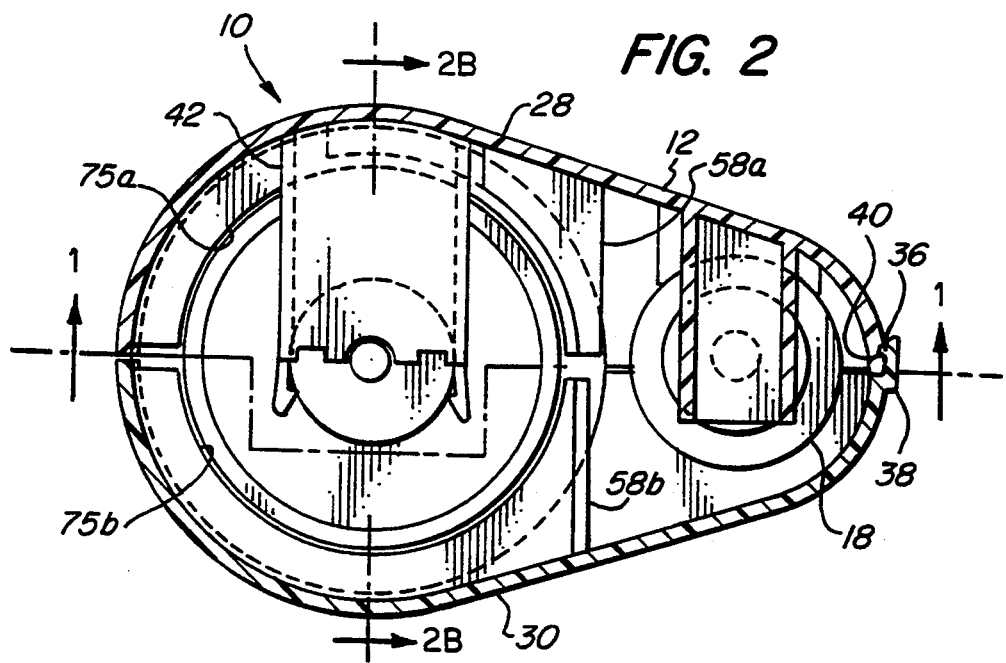
FIG. 2 is a top view, in partial cross section, of the dispenser of FIG. 1.
Figure 2A:
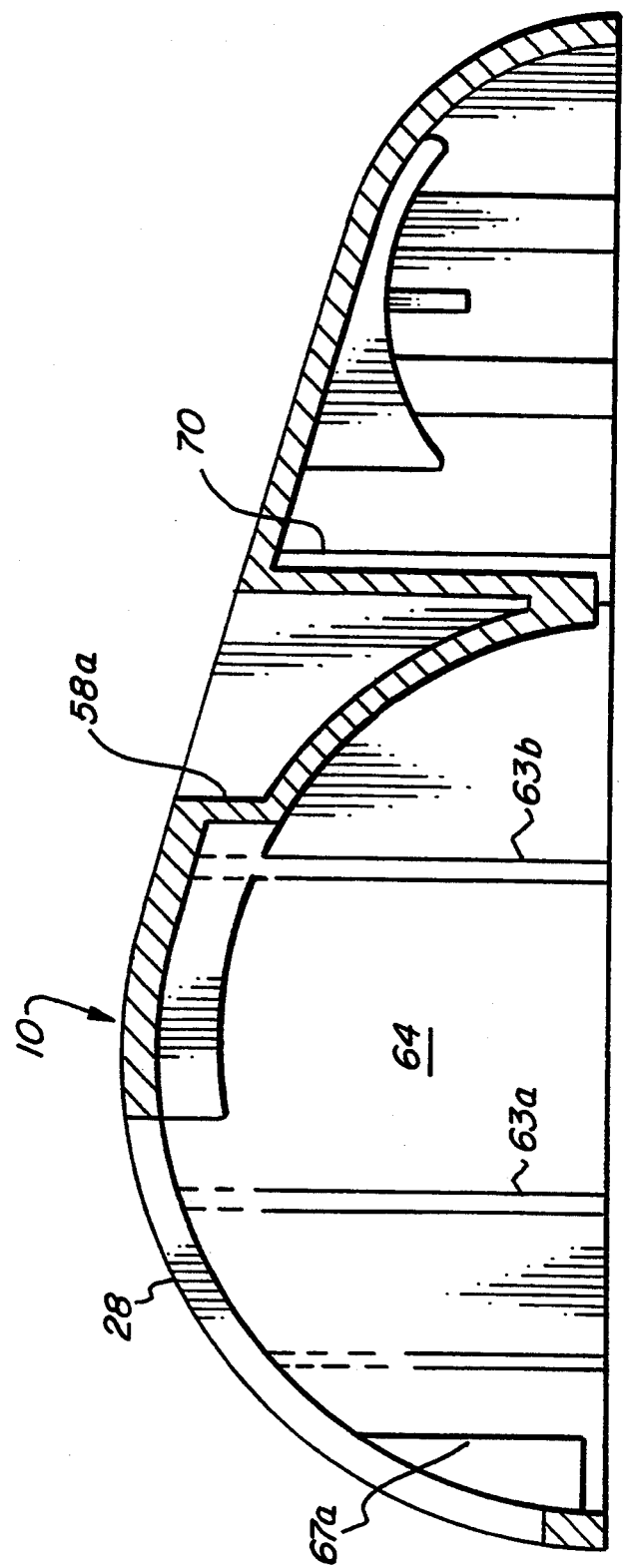
FIG. 2A is a partial cross sectional view of a portion of the dispenser shown in FIG. 1, taken along line 2A—2A with the cartridge removed for clarity.

As shown in FIG. 1, front side 30 (shown in FIG. 5) of housing 12 can be hinged at, preferably, two pivot points 34a, 34b. As shown in FIGS. 2, 4, front panel 30 is secured to back side 28 to close housing 12 by inserting tab 36 of latch 38 into notch 40.

As shown in FIGS. 2, 3, 4, 9, front side 30 and back side 28 can be designed to have the same or a different housing curvature, as desired. Front side 30 can, as desired, be straight, curved or any other suitable shape that is aesthetically appealing or desirable. Housing 12 may be given different appearances by attaching various different front panels 30 to housing 12 at 34a, 34b. In the drawings, front side 30 and back side 28 have generally the same shape.

As shown in FIGS. 1, 3, 5, 6, housing 12 has at least one inlet vent and at least one outlet vent. Most preferably, housing 12 has a plurality of substantially parallel vents 14a, 14b, 14c, 14d, 14e, 14a', 14b', 14c', 14d', 14e' which extend generally about one end 35 of housing 12. Preferably, vents 14a, 14b, 14c, 14d, 14e extend partially about front side 30, while vents 14a', 14b', 14c', 14d', 14e' extend partially about back side 28. Vents 14a, 14b, 14c, 14d, 14e, 14a', 14b', 14c', 14d', 14e' may extend any length about end 35 of housing 12, however, the length of vents 14a, 14b, 14c, 14d, 14e, 14a', 14b', 14c', 14d', 14e' should advantageously be maximized in order to maximize dispersal of the fragrance outside dispenser 10. Vents 14a, 14b, 14c, 14d, 14e, 14a', 14b', 14c', 14d', 14e' preferably extend all about those portions of housing 12 which do not rest adjacent to a supporting wall and which do not surround battery 18. Preferably, vents 14a, 14b, 14c, 14d, 14e, 14a', 14b', 14c', 14d', 14e' are disposed at least one hundred ninety degrees about housing 12, and preferably about one hundred ninety degrees to two hundred thirty degrees about housing 12. Most preferably, vents 14a, 14b, 14c, 14d, 14e, 14a', 14b', 14c', 14d', 14e' extend about two hundred ten degrees around the perimeter of housing 12.

Housing 12 has bracket 42, shown in FIG. 2, which secures motor 37 for operating fan 16 to inner surface of rear wall 28 of housing 12, as shown in FIG. 1. Any suitable motor can be used, such as the one manufactured and marketed by Mabuchi Motor America Corp. having part number RF-330TK-07800.

Fan 16 is preferably a centrifugal fan because of its ability to draw air into it, and then radially outward, thus permitting fan 16 to be disposed relatively closely to the vaporizable substance while not blowing air directly onto the vaporizable substance. Suitable centrifugal fans are commercially available, such as one manufactured by Advanced Air, Inc. of Riviera Beach, Fla. As shown in FIG. 1, fan 16 includes outer squirrel cage housing 46 which has cover 48, bottom rim 50, and vertical supports such as 52a, 52b extending therebetween. Uppermost portion 54 of fan 16 is adjacent uppermost portion 56 of vents 14a, 14b, 14c, 14d, 14e, 14a', 14b', 14c', 14d', 14e'. In the drawings, fan 16 lies substantially beside uppermost vents 14a, 14b, 14c, 14a', 14b', 14c'.

Fan 16 is electrically connected to removable battery 18, which is separated in housing 12 from fan 16 by walls 58a, 58b. See FIG. 2. Any suitable battery can be used, depending on motor 37 and fan 16, but a one and one-half volt battery, size D, is preferred. Battery 18 is designed to operate fan 16 continuously after being operably connected. Battery 18 and fan 16 could, however, be designed to operate fan 16 intermittently. Battery 18 could also be operated by a timer, if so desired.

As shown in FIG. 1, cartridge 20, having housing 60 and a hollow chamber (not shown), rests upon at least two elongated ribs 63a, 63b (also shown in FIG. 2A) projecting from uppermost surface 64 of bottom panel 26 of housing 12. Any suitable cartridge can be used such as the one previously disclosed by applicant in U.S. Pat. No. 5,230,867 entitled "Extended Release Fragrance Dispensing Cartridge." That patent is hereby incorporated by reference. Cartridge 20 may contain a fragrant oil-soaked pad (not shown) sealed within its hollow chamber by an air-permeable membrane (not shown) attached to shoulder 68. The density, permeability, and fiber characteristics of the pad and membrane are selected to achieve extended life while maintaining a desirable air freshening performance, as described in applicant's aforementioned patent.

The pad in the hollow chamber of cartridge 20 may contain any suitable vaporizable substance, preferably an odorous substance such as an oil or gel. Generally, an organic oil-based perfume is used. However, depending on cost and scent strength, it may be appropriate to mix the perfume with an odorless extender. A suitable extender for purposes of the present invention when aromatic organic oil-based perfumes are used, is Isopar®, an odorless mineral oil. Isopar® is a registered trademark owned by EXXON Corporation, New York, N.Y.

Figure 2B:
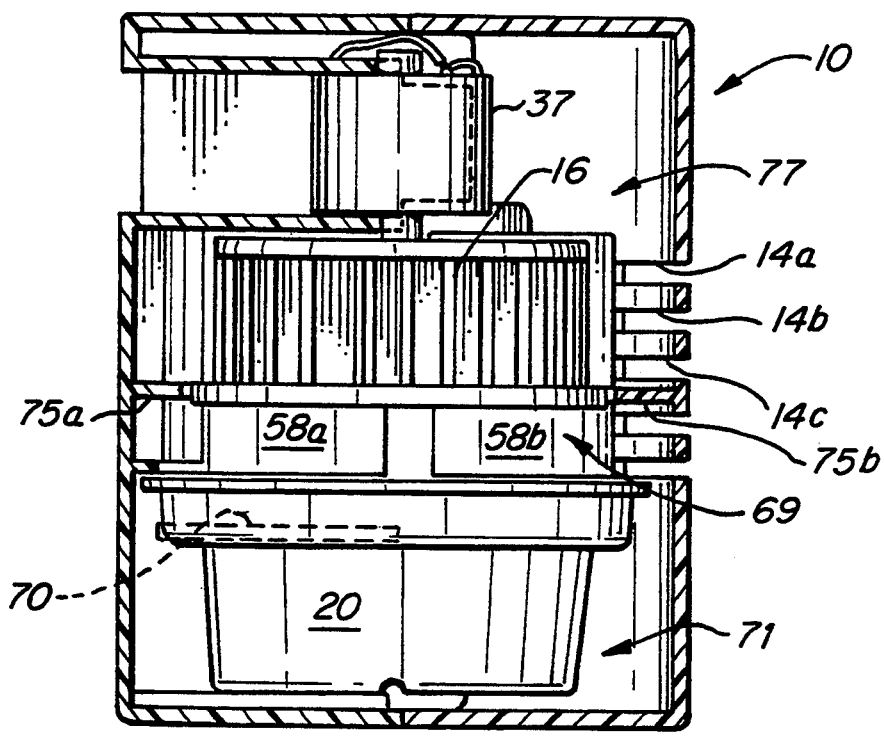
FIG. 2B is a cross sectional view of the dispenser shown in FIG. 2, taken along line 2B—2B.

As shown in FIG. 1, rim 66 of cartridge 20 is complimentarily received by a shelf 67a (shown in FIG. 2A) projecting from an inner surface of rear panel 28. Another shelf (not shown) preferably projects from an inner surface of front surface 30 of dispenser housing 12 to cooperate with shelf 67a to form a partial seal with rim 66. Preferably, at least two shelves, such as 67a are used, although as many shelves, or ribs, should be used so as to form a desired seal. Rim 66 and shelf 67a cooperate to form a boundary between substantially two compartments, sometimes referred to as a lower and middle cylindrical chamber, 71, 69, respectively, in housing 12. As shown in FIGS. 1, 2B, the middle compartment 69 lies substantially above shelf 67a and adjacent vents 14d, 14e, 14d', 14e'. The lower, or second, compartment 71 lies substantially below shelf 67a. Rim 66 and shelf 67a further cooperate such that air ingressing through inlet vents 14d, 14e, 14d', 14e' is capable of traveling generally towards fan 16, with little ability to travel in any other direction. Shelf 67a is preferably designed such that it contacts rim 66 and forms a seal with rim 66, although any suitable design can be used which substantially prevents or interferes with the flow of air in any direction other than towards fan 16.

At least two upper ribs 75a, 75b (shown in FIGS. 2, 2B) cooperate with a lower portion of fan housing 46 to form substantially a boundary between middle chamber 69 and upper chamber 77 (shown in FIGS. 1, 2B). Ribs 75a, 75b cooperate with housing 46 such that air flowing through middle compartment 69 has little ability to flow into upper chamber 77 except through fan 16. It should be understood that, although two ribs 75a, 75b are shown, many ribs could be used so long as a desirable seal between fan 16 and an inner surface of housing 12 is obtained.

Shelves and ribs projecting inwardly from housing 12 generally define the boundaries of each compartment or chamber. Lower chamber 71 has upper boundary defined substantially by lower surface of shelf 67a and lower boundary defined generally by upper surface 64 of bottom panel 26. See FIGS. 1, 2, 2A. Middle chamber 69 has lower boundary generally defined by upper surface of shelf 67a and upper boundary defined generally by lower surface of ribs 75a, 75b. See FIGS. 1, 2B. Upper chamber 77 has lower boundary defined generally by upper surface of ribs 75a, 75b and upper boundary defined substantially by lower surface 44 of top panel 24. Each chamber 69, 71, 77 is substantially bounded on one side by end 35 of housing 12 and on the other side by walls 58a, 58b.

Shoulder 68 of cartridge 20 acts cooperatively with stake 70 (shown in FIGS. 1, 2A), protruding from housing 12, to securely position cartridge 20 within housing 12. Shelf 67a also acts to prevent movement of cartridge 20 within housing 12. As such, cartridge 20 has relatively little ability to move freely even when disturbed.

Cartridge 20 is disposed within housing 12 under inlet vents 14d, 14e, 14d', 14e' and outlet vents 14a, 14b, 14c, 14a', 14b', 14c'. Rim 66, or uppermost portion of cartridge 20, lies substantially adjacent lowermost portion 72 of vents 14d, 14e, 14d', 14e'. See FIG. 1.

In operation, battery 18 is operably connected to fan 16. Cartridge 20 containing a vaporizable fragrance is placed on ribs 63a, 63b of upper surface 64 of bottom panel 26 below fan 16. Front panel 30 of housing 12 is then closed by securely latching tab 36 of latch 38 into notch 40. See FIGS. 1, 2, 2A, 4.

When fan 16 is operational, fan 16 draws air into housing 12 substantially through lower inlet vents 14d, 14e, 14d', 14e'. Fan 16 pulls air at least partially across cartridge 20 causing the oil or gel to be vaporized, pulls the air upward through housing 12 and into fan 16, and directs the air radially outward substantially through the uppermost outlet vents 14a, 14b, 14c, 14a', 14b', 14c'. As such, air flow movement is generally confined within middle and upper chambers 69, 77.

When air is drawn into inlet vents 14d, 14e, 14d', 14e', shelf 67a generally prevents air from flowing into lower compartment 71. Upper ribs 75a, 75b generally cooperate with fan housing 46 to prevent, or at least interfere with, air flow into upper chamber 77, except through fan 16.

Because centrifugal fan 16 pulls air upward and across cartridge 20, the fragrance contained in cartridge 20 is not vaporized as quickly as compared to a fan (not shown) which blows air directly down and onto cartridge 20. Because fan 16 pulls air upward from cartridge 20, rather than directly down onto cartridge 20 as shown in the prior art, the cartridge 20 and fan 16 can be placed in closer proximity to each other, thus reducing the overall size of dispenser 10.

Battery 18 and cartridge 20 can be replaced separately or as a unit (not shown). Because both battery 18 and cartridge 20 have a useful life of approximately the same length of time, which is approximately thirty days, it is oftentimes desirable to replace them simultaneously. Because front panel 30 of housing 12 is hinged, battery 18 and cartridge 20 can be easily replaced without removing dispenser 10 from a supporting wall.

It should be understood by those skilled in the art that obvious modifications can be made without departing from the spirit of the invention. Accordingly, reference should be made primarily to the accompanying claims, rather than the foregoing specification, to determine the scope of the invention.

We claim:

1. A dispenser for a vaporizable substance, comprising:
    a housing, the housing having at least one inlet vent and at least one outlet vent extending about the housing, the housing having at least one wall having an inner surface, and at least one shelf projecting from the inner surface of the wall of the housing, the shelf substantially defining a boundary between a lower, and a middle compartment;

a cartridge containing a vaporizable substance disposed within the housing, the cartridge further comprising a rim, the rim and shelf being adapted so as to prevent air flow into the lower compartment; and means for creating a flow of air within the housing between the inlet vent and the outlet vent such that air flows in the inlet vent, passes at least partially across the vaporizable substance, and flows radially out the outlet vent.

2. The dispenser for a vaporizable substance of claim 1, the housing further comprising an upper rib projecting from the inner surface of the wall, the air flow means further comprising a housing, the upper rib and the air flow means housing cooperating to substantially form a boundary between the middle compartment and an upper compartment, the upper rib and the air flow means housing being adapted so as to interfere with air flow into the upper compartment.

3. The dispenser for a vaporizable substance of claim 1, the air flow means comprising a centrifugal fan.

4. The dispenser for a vaporizable substance of claim 1, the housing further comprising two ends and at least one wall inside the housing between the two ends, the air flow means comprising a fan and a battery for energizing the fan, the battery being located on one side of the wall and the cartridge and fan being located on the opposite side of the wall.

5. The dispenser for a vaporizable substance of claim 1, the cartridge having an uppermost portion, the air flow means having an uppermost portion, the vents having a lowermost and an uppermost portion, the lowermost portion of the vents located substantially adjacent to the uppermost portion of the cartridge, and the uppermost portion of the vents located substantially adjacent to the uppermost portion of the air flow means.

6. The dispenser for a vaporizable substance of claim 1, further comprising a plurality of inlet vents and a plurality of outlet vents.

7. The dispenser for a vaporizable substance of claim 1, wherein the vents extend approximately one hundred ninety degrees to two hundred thirty degrees about the perimeter of the housing.

8. A dispenser for a vaporizable substance, comprising:

a housing having a first end and a second end;

at least one inlet vent extending about the first end of the housing, the inlet vent having a top and a bottom;

at least one outlet vent extending about the first end of the housing, the outlet vent being positioned above the inlet vent;

a cartridge containing a vaporizable substance disposed within the housing, the cartridge having a rim, the rim of the cartridge being positioned no higher than the bottom of the inlet vent; and means for creating a flow of air within the housing between the inlet vent and the outlet vent such that the air flows in the inlet vent, passes at least partially across the vaporizable substance, flows upwardly towards the air flow means, and flows radially out the outlet vent.

9. The dispenser for a vaporizable substance of claim 8, the air flow means comprising a centrifugal fan.

10. The dispenser for a vaporizable substance of claim 8, the cartridge further comprising a rim, the housing further comprising a wall having an inner surface and at least one shelf adjacent the rim and projecting from the inner surface of the wall, the shelf substantially defining a boundary between a middle and a lower compartment, the shelf and rim cooperating to substantially prevent the flow of air into the lower compartment.

11. The dispenser for a vaporizable substance of claim 10, the air flow means further comprising a housing, the dispenser housing further comprising at least one upper rib adjacent the air flow means housing, the rib projecting from the inner surface of the wall of the housing and substantially defining a boundary between an upper compartment and the middle compartment.

12. The dispenser for a vaporizable substance of claim 11, the dispenser housing further comprising a plurality of ribs.

13. The dispenser for a vaporizable substance of claim 8, the housing further comprising a wall between the two ends, the air flow means comprising a fan and a battery for energizing the fan, the battery being located on one side of the wall and the cartridge and fan being located on the opposite side of the wall.

14. The dispenser for a vaporizable substance of claim 8, the cartridge having an uppermost portion, the air flow means having an uppermost portion, the vents having a lowermost and an uppermost portion, the lowermost portion of the vents located substantially adjacent to the uppermost portion of the cartridge, and the uppermost portion of the vents located substantially adjacent to the uppermost portion of the air flow means.

15. The dispenser for a vaporizable substance of claim 8, further comprising a plurality of inlet vents and a plurality of outlet vents.

16. The dispenser for a vaporizable substance of claim 8, wherein the vents extend approximately one hundred ninety degrees to two hundred thirty degrees about the perimeter of the housing.

17. A dispenser for a vaporizable substance, comprising:

a dispenser housing having at least one inlet vent and at least one outlet vent, the dispenser housing further having a top, a bottom, and a wall extending upward from the bottom of the dispenser housing, and a lower shelf and an upper shelf projecting from the wall;

a cartridge, having a rim, disposed within the dispenser housing;

a fan, having a fan housing, disposed inside the dispenser housing for creating air flow, the fan housing having an uppermost portion and a bottom; and an upper compartment bounded by the upper shelf and the top of the dispenser housing; and a middle compartment bounded by the upper shelf and the lower shelf, the upper shelf positioned adjacent to the bottom of the fan housing, the upper shelf and the bottom of the fan housing cooperating such that air flow primarily enters the upper compartment through the fan housing.

18. The dispenser for a vaporizable substance of claim 17, the housing having a wall having an inner surface and a shelf, the shelf projecting from the inner surface so as to form substantially a boundary between a lower and middle chamber.

19. The dispenser for a vaporizable substance of claim 17, the housing having a wall having an inner surface and a rib, the rib projecting from the inner surface so as to form substantially a boundary between a middle and upper chamber.

* * * * *